United States Patent [19]
Takashima et al.

[11] Patent Number: 5,837,853
[45] Date of Patent: Nov. 17, 1998

[54] PREVENTIVE OR THERAPEUTIC AGENTS FOR ALZHEIMERS DISEASE A SCREENING METHOD OF ALZHEIMERS DISEASE AND TAU-PROTEIN KINASE I ORIGINATED FROM HUMAN BEING

[75] Inventors: Akihiko Takashima; Toshimitsu Hoshino, both of Machida; Kazutomo Imahori, Meguro-ku; Ken-ichi Saito, Asao-ku; Akiko Shiratsuchi, Sagamihara; Showbu Sato, Machida, all of Japan

[73] Assignee: Mitsubishi Chemical Corporation, Tokyo, Japan

[21] Appl. No.: 602,264

[22] Filed: Feb. 20, 1996

Related U.S. Application Data

[63] Continuation of Ser. No. 204,091, Mar. 2, 1994, abandoned.

[30] Foreign Application Priority Data

| Mar. 20, 1993 | [JP] | Japan | 5-041160 |
| Mar. 22, 1993 | [JP] | Japan | 5-085143 |
| Aug. 2, 1993 | [JP] | Japan | 5-191246 |

[51] Int. Cl.$^6$ ............... C07H 21/02; C07H 21/04
[52] U.S. Cl. ............ 536/24.5; 536/23.1; 536/24.31; 435/6; 435/91.1; 435/353
[58] Field of Search ............ 514/44; 536/23.1, 536/24.31, 24.5; 435/6, 91.1, 353

[56] References Cited

PUBLICATIONS

A. Caceres et al., "The effect of Tau Antisense Oligonucleotides on Neurite Formation of Cultured Cerebellar Macroneurons", The Journal of Neuroscience, vol. 11, No. 6, pp. 1515–1523, Jun. 11, 1991.

K. Ishiguro et al., "Tau Protein Kinase I Converts Normal Tau Protein into A68–like Component of Paired Helical Filaments", The Journal of Biological Chemistry, vol. 267, No. 15, pp. 10897–10901, May 25, 1992.

K. Ishiguro et al., "Phosphorylation Sites on Tau by Tau Protein Kinase I, A Bovine Derived Kinase Generating an Epitope of Paired Helical Filaments", Neuroscience Letters, vol. 148, No. 1 and 2, pp. 202–206, Dec. 14, 1992.

A. Takashima et al., "Tau Protein Kinase I is Essential for Amyloid β–Protein–Induced Nerotoxicity", Proc. Natl. Acad. Sci., vol. 90, No. 16, pp. 7789–7793, Aug. 15, 1993.

Tseng et al (1994) Cancer Gene Therapy 1, 65–71.

Weiss (1991) Science News 139, 108–109.

Woodgett (1990) EMBO J. 9, 2431–2438.

Alma et al (1991) Drugs Exptl. Clin. Res. XVII, 575–579.

Ishiguro et al (1993) FEBS Lett 325, 167–172.

Bramblett et al (1992) Lab. Invest. 66, 212–222.

*Primary Examiner*—John Leguyader
*Assistant Examiner*—Andrew Wang
*Attorney, Agent, or Firm*—Wenderoth, Lind & Ponack, L.L.P.

[57] ABSTRACT

A preventive or therapeutic agent for Alzheimer's disease which comprises a substance exhibiting an inhibitory action to tau-protein kinase I as an effective component is provided. A pharmaceutical composition comprising said agent and a method of inhibiting neuronal cell death in the brain are also provided.

8 Claims, 2 Drawing Sheets

FIG. 2

Comparison of amino acid sequence between human and rat TPKI's

```
Human  MSGRPRTTSFAESCKPVQQPSAFGSMKVSRDKDGSKVTTVVATPGQGPDRPQEVSYTDTKLIGNGSFGVV  70
Rat    MSGRPRTTSFAESCKPVQQPSAFGSMKVSRDKDGSKVTTVVATPGQGPDRPQEVSYTDTKVIGNGSFGVV  70
                                                                    *

Human  YQAKLCDSGELVAIKKVLQDKRFKNRELQIMRKLDHCNIVRLRYFFYSSGEKKDEVYLNLVLDYVPETVY  140
Rat    YQAKLCDSGELVAIKKVLQDKRFKNRELQIMRKLDHCNIVRLRYFFYSSGEKKDEVYLNLVLDYVPETVY  140

Human  RVARHYSRAKQTLPVIYVKLYMYQLFRSLAYIHSFGICHRDIKPQNLLLDPDTAVLKLCDFGSAKQLVRG  210
Rat    RVARHYSRAKQTLPVIYVKLYMYQLFRSLAYIHSFGICHRDIKPQNLLLDPDTAVLKLCDFGSAKQLVRG  210

Human  EPNVSYICSRYYRAPELIFGATDYTSSIDVWSAGCVLAELLLGQPIFPGDSGVDQLVEIIKVLGTPTREQ  280
Rat    EPNVSYICSRYYRAPELIFGATDYTSSIDVWSAGCVLAELLLGQPIFPGDSGVDQLVEIIKVLGTPTREQ  280

Human  IREMNPNYTEFKFPQIKAHPWTKVFRPRTPPEAIALCSRLLEYTPTARLTPLEACAHSFFDELRDPNVKL  350
Rat    IREMNPNYTEFKFPQIKAHPWTKVFRPRTPPEAIALCSRLLEYTPTARLTPLEACAHSFFDELRDPNVKL  350

Human  PNGRDTPALFNFTTQELSSNPPLATLIPPHARIQAAASTPTNATAASDANTGDRGQTNNAASASASNST  420
Rat    PNGRDTPALFNFTTQELSSNPPLATLIPPHARIQAAASPPANATAASDTNAGDRGQTNNAASASASNST  420
                                            *      **
```

PREVENTIVE OR THERAPEUTIC AGENTS FOR ALZHEIMERS DISEASE A SCREENING METHOD OF ALZHEIMERS DISEASE AND TAU-PROTEIN KINASE I ORIGINATED FROM HUMAN BEING

This application is a continuation of now abandoned application, Ser. No. 08/204,091, filed Mar. 2, 1994.

BACKGROUND OF THE INVENTION

1. Field of the Invention

The present invention relates to a preventive or a therapeutic agent for Alzheimer's disease, a method of screening Alzheimer's disease and tau-protein kinase I which is originated from a human being. More particularly, it relates to a preventive or a therapeutic agent for Alzheimer's disease using a tau-protein kinase I inhibitor; a method of screening for a preventive or a therapeutic agent for Alzheimer's disease utilizing an amyloid beta-protein; a human-originated tau-protein kinase I which phosphorylates tau-protein, partial peptides thereof or peptides similar thereto; a gene which encodes the kinase; and a method of producing the same.

2. Description of Related Art

Alzheimer's disease is a progressive dementia which develops in late middle ages (45 to 65 years old) and its etiological changes are shrinkage of cerebral cortex due to a neuronal cell loss and degeneration of the neurons while, from the pathological view, many senile plaques and neurofibrillary tangles are noted in the brain. There is no pathologically substantial difference between the disease and senile dementia caused by the so-called natural aging which develops in the senile period of 65 years and older ages and, therefore, this disease is called senile dementia of Alzheimer type.

The numbers of the patients having this disease are increasing with an increase in the population of aged people, and so the disease is becoming an increasing health concern of society. There are various theories on the cause of this disease, but the cause is still ambiguous and, accordingly, there has been a demand for more information about the disease.

It has been known that the quantities of insoluable substances which appear in the two pathological changes which are characteristic of Alzheimer's disease and senile dementia of Alzheimer type are well correlated with the degree of cognitive impairment. Accordingly, studies for clarifying the cause of those diseases by clarifying, at a molecular level, the accumulated insoluble substances resulting in those two pathological changes have been carried out since the first half of the 1980's.

It has been clarified already that a main component of the senile plaques which is one of those pathological changes is amyloid beta-protein (hereinafter, it may be abbreviated as "AβP") [Annu. Rev. Neurosci., 12, 463–490 (1989)]. A neurofibrillary tangle which is another pathological change is due to an accumulation of a double-stranded fibrous substance called PHF (paired helical filament) in the neurons and, recently, the components thereof have been identified as ubiquitin and tau-protein which is one of the microtubule-associated proteins characteristic to the brain [J. Biochem., 99, 1807–1810 (1986); Proc. Natl. Acad. Sci. USA, 83, 4913–4917 (1986)].

It is believed now that, in Alzheimer's disease, the amyloid beta-protein is extremely accumulated in the neurons and that, as a result of its correlation with the formation of PHF, death of the neurons results.

It has been known that the tau-protein (hereinafter, the protein may be abbreviated "tau") is usually a series of related proteins forming several bands at molecular weights of 48–65 kd on SDS polyacrylamide gel electrophoresis and that it promotes the formation of microtubules.

It has been proved already by the use of polyclonal antibody to PHF [anti-ptau: J. Biolchem. 99, 1807–1810 (1986)] and also of monoclonal antibody [tau-1 antibody; Proc. Natl. Acad. Asic. USA, 83, 4913–4917(1986)] that the tau which is incorporated in the PHF of the brain of Alzheimer's disease patient is extremely phosphorylated as compared with the normal one.

The present inventors have isolated an enzyme which catalyzes such an abnormal phosphorylation, named it "tau-protein kinase I" (hereinafter, it may be abbreviated as "TPK-I") and clarified its biochemical properties [Seikagaku, vol. 64, no. 5, page 308 (1992)] . The inventors have further cloned the cDNA of rat TPK-I from the cDNA library of cerebral cortex of rats based upon the partial amino acid sequence of TPK-I, whereby the base sequence has been determined and the amino acid sequence has been proposed (SEQ. I.D. NO: 2 in the Sequence Listing; Japanese Patent Application 177241/92, FEBS Lett., 325, 167–172 (1993)).

As a result, it has been confirmed that the primary structure of the rat TPK-I is identical with that of the enzyme which is known as rat GSK-3β (glycogen syntase kinase 30β) [EMBO J., 9, 2431–2438 (1990)]. However, in studies for drugs which are effective for the prevention or the therapy of human diseases, it is known that the primary structures which are targets for the drug usually vary depending upon the animal species. Therefore, there are many cases where the interaction between the drug and the protein (in other words, sensitivity and effectiveness of the drug) greatly differs depending upon the animal species [e.g. Nature, 360, 161 (1992)]. Thus, in order to find drugs which are really effective in a human being, it is desired that research be carried out using proteins which are originated from human being. Particularly in the case of finding drugs effective for diseases which have not been found in animals other than human being such as Alzheimer's disease, it is believed to be essential to use proteins originated from human being. However, there has been no report on the separation and purification of TPK-I (or GSK-3β) from human tissues and, moreover, there has been no report on a gene (cDNA) which encodes human TPK-I (or GSK-3β).

SUMMARY OF THE INVENTION

An object of the present invention is to clarify the correlation between the death of neurons and accumulation of PHF and amyloid beta-protein characteristically found in the brains of Alzheimer's disease to apply it to the clarification of the cause of Alzheimer's disease and further to discover preventive or therapeutic agents therefore.

Another object of the present invention is to clarify the structure of the human-originated TPK-I (which is essential for the progress of investigations for such drugs) on a molecular biological basis and to offer a method of producing it by means of gene technology.

The present inventors have carried out investigations for achieving the above-given objects and confirmed that, when amyloid beta-protein acts on the neurons in the brain, activity of TPK-I significantly increases whereupon the extremely phosphorylated tau-protein found in PHF of the brains of Alzheimer's disease results. Moreover, the neurons are killed, and the above-mentioned increase in the TPK-I activity and neuronal cell death in the brain is inhibited by treatment with the antisense oligonucleotide of TPK-I.

In addition, with a view that the accumulation of PHF results in the degeneration of neurons in the brains of Alzheimer's disease patients and successively induces death, the present inventors have for the first time cloned the gene (which encodes the human-originated TPK-I which is thought to be a key enzyme for the PHF formation) from the cDNA library of human fetus brain, whereupon its primary structure is determined. A method for constant supply (or production) of the human-originated TPK-I has also been established.

The present invention has been achieved as a result of the above-given findings followed by further investigations, and its characteristic features are as follows:

(1) a preventive or a therapeutic agent for Alzheimer's disease, which comprises a substance exhibiting an inhibitory action on tau-protein kinase I as an effective component;

(2) a preventive or a therapeutic agent for Alzheimer's disease, which comprises an antisense oligonucleotide capable of hybridizing with mRNA or DNA of tau-protein kinase I as an effective component;

(3) a pharmaceutical composition for prevention or therapy of Alzheimer's disease, which comprises a substance exhibiting an inhibitory action on tau-protein kinase I and a pharmaceutically acceptable carrier;

(4) a pharmaceutical composition for prevention or therapy of Alzheimer's disease, which comprises an antisense oligonucleotide capable of hybridizing with mRNA and DNA of tau-protein kinase I;

(5) a method of screening for a preventive or a therapeutic agent for Alzheimer's disease in which, when amyloid beta-protein, nerve cells and a drug which is presumed to be effective as a preventive or a therapeutic agent for Alzheimer's disease are incubated and the death of said nerve cells is inhibited, then said drug is judged to be effective as a preventive or a therapeutic agent for Alzheimer's disease;

(6) a method of inhibiting the death of neurons in the brain, characterized in that a substance which exhibits an inhibitory action on tau-protein kinase I in the neuron in the brain is applied;

(7) a method of inhibiting the death of neurons in the brain, characterized in that an antisense oligonucleotide which is capable of hybridizing with mRNA or DNA of tau-protein kinase I is applied to the cranial nerve cells;

(8) human-originated tau-protein kinase I characterized in being represented by an amino acid sequence given in the SEQ. I.D. NO: 1 of the attached Sequence Listing or a partial sequence thereof;

(9) gene which encodes the human-originated tau-protein kinase I which is represented by the amino acid sequence given in the SEQ. I.D. NO: 1 of the attached Sequence Listing or a partial sequence thereof;

(10) recombinant human-originated tau-protein kinase I;

(11) recombinant vector which is capable of expressing the recombinant human-originated tau-protein kinase I;

(12) a transformant which is obtained by transformation of host cells by a recombinant vector which is capable of expressing the recombinant human-originated tau-protein kinase I; and

(13) a method of producing a recombinant human-originated tau-protein kinase I, characterized in that a transformant obtained by transformation of host cells by a recombinant vector which is capable of expressing the recombinant human-originated tau-protein kinase I is incubated and then the recombinant human-originated tau-protein kinase I is collected from said culture.

The present invention will be further illustrated hereinbelow.

BRIEF DESCRIPTION OF THE DRAWINGS

FIG. 2 is a drawing which shows a comparison of the amino acid sequences of human TPK-I and rat TPK-I. In the drawing, each amino acid is represented by a single letter.

DETAILED DESCRIPTION OF THE PREFERRED EMBODIMENT(S)

Figure 1:
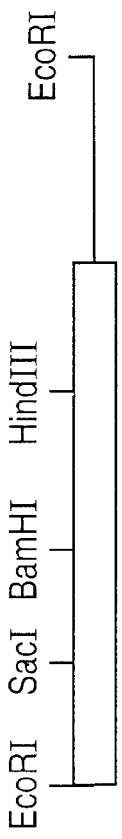
FIG. 1 is a drawing which shows the restriction enzyme map of human TPK-I.
Figure 1:
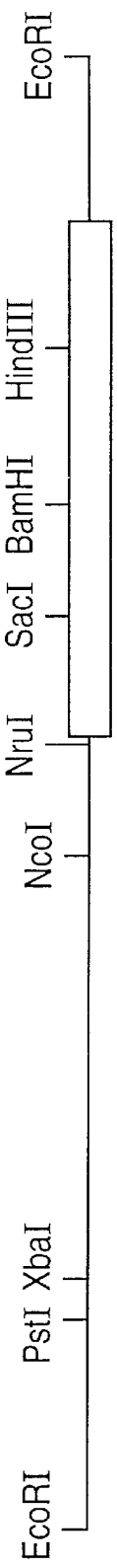

With regard to the substance which exhibits an inhibitory action on tau-protein kinase I in the present invention, any substance will do provided that, when said substance is incubated together with nerve cells and amyloid beta-protein, death of said nerve cells is inhibited. For example, it is a chemically synthesized substance, a substance which is extracted from living cells of microorganisms, etc.

Further, in accordance with the present invention, an antisense oligonucleotide (hereinafter, it may be abbreviated as "TPK-I antisense oligonucleotide") which is capable of hybridizing with mRNA or DNA of TPK-I is used for prevention or therapy of Alzheimer's disease.

Antisense oligonucleotides are capable of inhibiting protein synthesis at the gene level and, therefore, have been receiving attention in the medical field as a synthetic inhibitor for proteins causing disease. The principle is that, when the antisense RNA or the antisense DNA forms a base pair with mRNA in a sense sequence, spread of the gene information is interrupted and synthesis of protein which is the final product is inhibited [Igaku no Ayumi, vol.162, no.13, 909–911(1992)].

With regard to the TPK-I antisense oligonucleotide applied in the present invention, anything will do provided that it is capable of hybridizing with mRNA or DNA of TPK-I and that it has a sequence for inhibiting the synthesis of TPK-I by, for example, inhibition of transcription, inhibition of splicing of pre-mRNA, inhibition of mRNA septum transmission, inhibition of translation, etc. Usually, an antisense oligonucleotide comprising about 15 to 30 nucleotides is used.

Furthermore, the antisense oligonucleotides applicable are a phosphorothioate type in which an oxygen atom which is bonded by means of a double bond with a phosphorus atom at the phosphodiester bond connecting deoxyribonucleosides is substituted with a sulfur atom; a methyl phosphate type in which a methyl group is introduced instead of the sulfur atom; a phosphonate type without substitution; and an alpha-oligonucleotide type [Anticancer Drug Des. 6 (66), 606–646 (1991); Anticancer Research, 10, 1169–1182 (1990)]. In addition, in the present invention, it is not always necessary to use a nucleotide type in which a nucleoside derivative is bonded provided that the substance can form a hybrid with the aimed sequence. For example, the antisense compounds which are described in Antisense Research and Development, 1, 65–113 (1991), etc. may be used as well.

Specific examples of the TPK-I antisense oligonucleotides used in the present invention are TPK-I antisense oligonucleotide chain: 5'-TCTCGGTCGCCCCGACAT-3' (SEQ. I.D. NO: 5 of the Sequence Listing) which is complementary to TPK-I sense oligonucleotide chain: 5'-ATGTCGGGGCGACCGAGA-3' (SEQ. I.D. NO: 4 of the Sequence Listing) corresponding to the first six amino acid residues: Met-Ser-Gly-Arg-Pro-Arg in the translation initiating domain of TPK-I in the primary structure of the rat GSK-3β [same as the primary structure of the rat TPK-I (EQ. ID. No. 2 of the Sequence Listing) described in the above-referenced EMBO J., 9, 2431–2438(1990)]; the TPK-I antisense oligonucleotide chain: 5'-TCTGGGCCGCCCTGACAT-3' (SEQ. I.D. NO: 7 of the Sequence Listing) which is complementary to the TPK-I sense oligonucleotide chain: 5'-ATGTCAGGGCGGGCCCAGA-3' (SEQ. I.D. NO: 6 of the Sequence Listing) corresponding to the first six amino acid residues: Met-Ser-Gly-Arg-Pro-Arg in the translation initiating domain of TPK-I in the primary structure of human TPK-I (SEQ. I.D. NO: 1 of the Sequence Listing; also refer to the examples which will given below); and the like.

The above-mentioned TPK-I sense oligonucleotide and TPK-I antisense oligonucleotide can be easily synthesized by means of commercially-available automatic DNA synthesizers such as a DNA synthesizer manufactured by Applied Biosystems, or manufactured by MilliGen, etc. As mentioned already, the TPK-I antisense oligonucleotides of the present invention are not particularly limited to those having the above-given sequences provided that they are capable of hybridizing with mRNA or DNA of TPK-I and, so far as the hybrid-forming ability is not deteriorated, a part of the sequence may be substituted with any base. In addition, antisense oligonucleotides which are changed or modified for passing through a blood-brain barrier as described in Science, 259, 373–377 (1993) are included in the coverage of the present invention as well.

When the TPK-I antisense oligonucleotides or the substances having an inhibitory action on TPK-I as mentioned above are used as preventive or therapeutic agents for Alzheimer's disease, they may be made into preparations which satisfy the necessary requirements of the particular administering route together with usual carriers. For example, in the case of oral administration, preparations in the form of tablets, capsules, granules, diluted powder, liquid, etc. are prepared.

In preparing solid preparations for oral use, commonly-used fillers, binders and lubricants as well as colorants, disintegrating agents, etc. may be used. Examples of the fillers are lactose, starch, talc, magnesium stearate, crystalline cellulose, methyl cellulose, carboxymethyl cellulose, glycerol, sodium alginate, gum arabic, etc. Examples of the binders are polyvinylalcohol, polyvinyl ether, ethyl cellulose, gum arabic, shellac, white sugar, etc. Examples of the lubricants are magnesium stearate, talc, etc. Besides those, commonly-used ones may be used for the colorants, disintegrating agents, etc. as well. Tablets may be coated by known methods. Liquid preparations may be aqueous or oily suspensions, solutions, syrups, elixiers and the like and may be manufactured by commonly-used methods. In preparing injections, pH-adjusting agents, buffers, stabilizers, isotonic agents, local anesthetics, etc. may be added to TPK-I antisense oligonucleotides or the substances having an inhibitory action to TPK-I and subcutaneous, intramuscular or intravenous injections may be prepared by common methods. with regard to the bases for the manufacture of suppositories, oily ones such as cacao butter, polyethylene glycol, Witepsol (registered trade mark of Dynamite Nobel) may be used.

Doses of the preparations manufactured as such are not always the same but vary depending upon the symptoms, body weights, ages, etc. of the patients. Usually, however, the amount corresponding to about 1 to 1,000 mg/kg of said drug per day for adults will do and it is preferred to administer by dividing that for 1 to 4 times daily. In some instances, the administration may be carried out once daily to every several or more days.

Examples of the nerve cells used in the present invention are the neuron in the brain collected from mammals and the neuronal cell lines in which the nerve projections are extended by the induction of growth factors such as NGF (nerve growth factor; neurotrophic factor), IGF (insulin-like growth factor), etc. An example of the former is a culture prepared by incubation of tissues of hippocampus of mammals (such as rat) in a complete culture medium. Examples of the latter are PC 12 cells induced by NGF, FGF (fibroblast growth factor), EGF (epidermal growth factor), interleukin 6, etc. [Ann. Rev. Pharma col. Toxicol., 31, 205–228 (1991) ]; SH-SY5Y cells induced by IGF [The Journal of Cell Biology, 102, 1949–1954 (1986)]; and those which are disclosed in Cell Culture in the Neurosciences, New York: Plenum Press, pages 95–123 (1955) such as NGF-induced MJB cells, NMB cells, NGP cells, SK-N-SH-SY5Y cells, LAN-1 cells, KA-9 cells, IMR-32 cells and 5-bromodeoxyuridine-induced IMR-32 cells, NMB cells, NGP cells, etc.

Amyloid beta-protein is a main component of senile plaques of Alzheimer's disease and it has been known that said substance is composed of a peptide comprising the following 43 amino acid residues [Science, 250, 279–282 (1990) and Proc. Natl. Acad. Sci. USA, 87, 9020–9023 (1990)].

Amino Acid Sequence of Amyloid beta-Protein (SEQ. ID No. 3 of the Sequence Listing):

Asp Ala Glu Phe Arg His Asp Aer Gly Tyr Alu Val His His Gln Lys Leu Val Phe Phe Ala Glu Asp Val Gly Ser Asn Lys Gly Ala Ile Ile Gly Leu Met Val Gly Gly Val Val Ile Ala Thr

The present invention will be further illustrated hereinafter by an example on the behavior of hippocampus cells of rats and the phosphorylation activity of TPK-I when the hippocampus cells were treated with a certain amount of AβP and also with TPK-I sense oligonucleotide (hereinafter, referred to as "TPKI-sense") and TPK-I antisense oligonucleotide (hereinafter, referred to as "TPKI-antisense") as controls under certain conditions. When the present invention is carried out as a method of screening the preventive and the therapeutic agent of Alzheimer's disease, hippocampus cells of rat are used as the neurons and, as the agent presumed to be the preventive or the therapeutic agent, TPKI-sense or TPKI-antisense is used.

Certain amount of TPKI-antisense was added to the culture of the hippocampus cells at a certain temperature, then a certain amount of AβP was added thereto, the mixture was kept at a certain temperature and the living cell numbers with an elapse of time were measured by a method described in the examples which will be given below. For comparison, the living cell numbers were measured for the case in which only AβP was added followed by the same treatments and the case in which TPKI-antisense and AβP were added followed by the same treatments. The result showed that, as given in the examples below the living cell numbers when TPKI-antisense and AβP were added were significantly more than those when only AβP was added and when TPKI-sense and AβP were added, and that the TPKI-antisense has an action of inhibiting the death of the cells by AβP.

The results of the observations of the samples using a phase contrast microscope (magnifying power: 400) when TPKI-antisense and AβP were added to the cell culture followed by allowing to stand for 24 hours, when only AβP was added followed by allowing to stand for the same time, and when TPKI-sense and AβP were added followed by allowing to stand for the same time, showed that the cell toxicity by AβP was little, being similar to the controls only when TPKI-antisense was acted.

Further, the phosphorylation activities of tau-protein by TPKI after 24 hours were measured by the method given in the examples when only AβP was added and allowed to stand and when TPKI-antisense and AβP were added and allowed to stand same as above. The result was that, as shown in the examples given later, the phosphorylation activity of TPK-I when TPKI-antisense and AβP were added was about one half of that when only AβP was added and that TPKI-antisense exhibits an activity of inhibiting the phosphorylation activity of TPK-I.

Out of the above results, it may be concluded that, when the present invention is carried out as a method of screening the preventive and the therapeutic agent for Alzheimer's disease, TPKI-antisense is effective as a preventive and therapeutic agent. Incidentally, the effectiveness of the agents other than the TPK-I antisense oligonucleotide can be evaluated similarly.

Now, the method of obtaining the human-originated TPK-I and the method of production thereof will be illustrated.

The TPK-I originated from human being of the present invention may, for example, be manufactured as follows. Thus, microtubule fractions were obtained from an extract of human brain immediately after death by means of temperature-depending polymerization and depolymerization. Then, operations such as phosphocellulose column chromatography, gel filtration, hydroxyapatite column chromatography, S-Sepharose column chromatography, heparin column chromatography, etc. are combined according to a method by Uchida, et al. [Seikagaku, vol.64, no.5, page 308 (1992)] whereby pure protein is obtained. The (partial) primary structure of such a pure protein may be determined by conducting a conventional amino acid analysis. It is not easy to obtain human brain tissues in large quantities and it is difficult to purify the human TPK-I. By a method which will be given below, the gene of human TPK-I is cloned and the amino acid sequence is deduced therefrom whereby the primary structure is determined.

The human TPK-I of the present invention is a protein in which the primary structure is represented by the amino acids described in the SEQ. I.D. NO: 1 of the Sequence Listing (420 amino acid residues; molecular weight: 46,719; isoelectric point: 9.21) and alterations such as removal, substitution, modification or addition of some amino acids may be carried out within such a range that the functions (action, substrate specificity, etc.) will not be deteriorated.

The gene (cDNA) which encodes the above TPK-I may be cloned by a method in which the corresponding protein is purified from natural material, its partial amino acid sequence is determined and the DNA probe corresponding thereto is utilized; a method in which homology with the protein of the same species or the corresponding protein of the different animal species is utilized; a method in which an antibody which is specific to the corresponding protein is utilized; a method in which a detection of the specific function of the protein is utilized; etc. The present inventors have previously purified TPK-I from an extract of brain of rat or bovine and, depending upon the information of the partial amino acid sequence thereof, they cloned the rat TPK-IcDNA from the rat brain cDNA library (SEQ. I.D. NO: 2 of the Sequence Listing; Japanese Patent Application No. 177241/92, FEBS Lett., 325, 167–172 (1993)).

Usually, however, the homology of the primary structures of rats with human beings in the same protein is, in most cases, around 90% or more and, therefore, it is possible to clone human TPK-IcDNA from rat TPK-IcDNA by utilizing said homology. Thus, lamda-phage is infected to *Escherichia coli* by a method of Tomizawa, et al. ["Experiments in Bacteriophage" (Iwanami Shoten), pages 99–174 (1970)] from cDNA library containing the gene which encodes human TPK-I such as human fetus brain cDNA library followed by culturing. The plaques formed thereby were selected by a plaque hybridization method ["Molecular Cloning" Cold Spring Harbor Laboratory, pages 320–328 (1982)] using a rat TPK-ICDNA or DNA fragments having a partial structure thereof as a probe. The phage is promulgated from positive plaques by a method of Tomiza, et al., then DNA is prepared by a method of T. Maniatis, et al. ["Molecular Cloning", Cold Spring Harbor Laboratory, page 85 (1982)] or after subjecting to a subcloning if necessary, cleaved by a suitable restriction enzyme such as EcoRI and cloned to a plasmid such as pUC18 or pUC19. As such, cDNA of human TPK-I is prepared and its base sequence can be determined, for example, by a dideoxy method of Sanger, et al. [Proc. Natl. Acad. Sci. USA, 74, 5463 (1977)].

An example of the above-mentioned gene (cDNA) encoding the human-originated TPK-I is that which has a base sequence given in the SEQ. I.D. NO: 1 of the Sequence Listing.

In the human TPK-I prepared by the present invention, 5 amino acid residues were different out of the 420 amino acid residues in the amino acid sequence of the rat TPK-I and the homology in the bases in the translation domain was 92.5%.

The above-prepared human TPK-I or its partial peptides can be expressed and generated by means of gene recombination. Thus, the 5'-terminal of the human TPK-IcDNA or its fragment is modified or added with precursor gene, inserted into the downstream of the promoter of the expressed vector and then the vector is induced into host cells such as bacteria, yeasts, insect cells, animal cells, etc. The transformed host cells are cultured under a suitable condition whereby the recombinant human TPK-I is produced in or outside the cells.

Examples of the transformable host cells are bacteria (prokaryotic cells) such as *Escherchia coli* (K-12 strain), *Bacillus subtitlis,* etc.; yeasts such as *Saccharomyces cerevisiae;* insect cells such as ovary-originated cells (Sf9 cell strain) of Spodoptera spp.; and (mammalian) animal cells such as ovary-originated cells (CHO cells) of Chinese hamster, mouse C127 cells, kidney-originated cells (COS cells) of African green monkey, mouse L cells, mouse FM3A cells, kidney-originated cells (HEK cells, 293 cells) of human fetus, etc.

The expression vector which is suitably used contains a promoter at the position where a gene (cDNA) coding the human TPK-I or the DNA fragment thereof can be transcribed. For example, when cells are used as a host, it is preferred that the expression vector is composed of promoter, ribosome binding (SD) sequence, human TPK-I-encoding gene or fragment thereof, transcription terminating factor and promoter-controlling gene. Even when eukaryonic cells such as (mammalian) animal cells, insect cells, yeasts, etc. are used as host cells, the fundamental unit comprising the expression vector is the same as in the case of the above-mentioned bacteria.

Examples of the promoter when bacteria are used as host cells are those originated from *Escherichia coli,* phage, etc. such as lactose operon (lac), tryptophan-synthesizing enzyme (trp), lamda-phage $P_L$, *E. coli* T7 polymerase promoter and tac (hybrid promoter originated from trp and lac UV5). The examples in the case of yeasts are promoters of genes of enzymes such as phosphoglyceric acid kinase (PGK), glyceraldehyde-3-phosphoric acid dehydrogenase (GPD), repressible acidic phosphatase (PHQ5) and alcohol dehydrogenase 1 (ADH1). The examples in the case where insect cells are used as the host are the promoter of polyhedron gene of baculovirus, etc. The examples in the case of (mammalian) animal cells are SV40 initial promoter, SV40 late promoter, apolipoprotein E gene promoter, etc.

Examples of the ribosome binding sequence are those which are originated from *E. coli,* phage, etc. and those which are partially complementary to the base sequence of the 3'-terminal domain of 16S ribosome RNA.

Though the transcription terminating factor is not always necessary, it is preferred to have one which is rhop-independent such as lipoprotein terminator, trp operon terminator, etc.

With regard to the sequence of those factors necessary for the expression on the expression plasmid (vector), it is desired that they are placed in the order of promoter, SD sequence, human TPK-I-encoding gene or fragment thereof and transcription terminating factor from the 5'-upstream side.

Specific examples of the expression vectors satisfying those requirements in the case where bacteria are used as the host are pKK233-2 (manufactured by pharmacia) and pET3C [Gene, 56, 125 (1987)]. Expression vector pGEX series (pharmacia) which are expressed as a fused protein may be used as well in the same manner. When yeasts are used as a host, the vector in which the above-mentioned promoter (and, further, gene which complements the auxotropic mutant as a selected marker such as trp1 and leu2) is incorporated into YEp vector having a replication origin of 2 micron DNA is suitably used. In the case of insect cells, an example is Maxbac (trademark) which is a baculovirus expression system manual version 1.4 of Invitrogen. In the case of animal cells, those having the above-mentioned promoter and selective marker gene such as neomycin-resisting gene (Neo) and dihydrofolic acid reductase gene (DHFR) are suitably used. When eukaryonic cells are used as a host, a shuttle vector to *E. coli* may be used as well.

Transformation of host cells may be carried out by a conventional manner. Culture of the transformant may be carried out by a method of T. Maniatis, et al. described in "Molecular Cloning" Cold Spring Harbor Laboratory, 1982. Though the culture temperature is not always the same depending upon the conditions such as the host cells, a temperature of about 25° to 40° C. is suitable.

The human TPK-I produced by such host-vector systems can be purified by a series of purifying steps corresponding to the hosts and culturing conditions such as extraction from the host, salting-out and chromatography using various columns. In the case of column chromatography, the suitably-used ones are phosphocellulose column chromatography, hydroxyapatite column chromatography, S-Sepharose column chromatography, heparin column chromatography, blue Sepharose column chromatography, etc.

The recombinant human TPK-I prepared as such is capable of phosphorylating proteins described above as tau-protein, glycogen-synthesizing enzyme, protooncogene product c-jun, etc. and partial peptides thereof and the progress of the phosphorylation can be confirmed by, for example, the conditions as given below. Thus, the recombinant human TPK-I of the present invention is added, together with a suitable amount of the substrate protein, to a buffer of pH 5.0–8.0 containing 0.2–4.0 mM magnesium acetate and 0.2–4.0 mM adenosine triphosphate, the mixture is incubated at room temperature to 40° C. and the phosphorylation of the substrate protein is checked and determined by radiochemical, proteinochemical or immunochemical means. Consequently, when an agent is added to this reaction system and the resulting promotion or inhibition of the phosphorylation reaction is checked, it is possible to find the agent having a physiologically important effect whereby the investigation on the agent which is effective for the prevention or the therapy of human disease is now possible.

EXAMPLES

The present invention will be illustrated by way of the following examples though the present invention is not limited to those examples. Incidentally, judgement of the cytotoxity, measurement of the phosphorylation of tau-proten and immunohistochemistry by Alz-50 antibody were carried out in accordance with the following methods. Further, in each of the following examples, at least three independent experiments were carried out and the data were given by their average values.

Judgement of Cytotoxity:

Numbers of many normal and healthy cells were counted by a phase contrast microscope as an index of the living cells after the treatment. Normal cells mean those which have morphologically flat circumference and many nerve cell projections while the degenerated cells were judged by checking for irregular shape, degeneration of the neural projections, etc. Numbers of the living cells were counted in a well. In the standard culture liquid, the cell numbers were not less than 400 per well. The result was confirmed by an immunohistochemical means.

Measurement of Degree of Phosphorylation of tau-Protein:

Hippocampus cells were collected from the culture medium by washing with an ice-cooled phosphate buffer for three times. The cells were suspended in a buffer A (pH: 6.8) which contained 1 mM EGTA, 0.5 mM magnesium acetate and 20 mM 2- (N-morpholino) -ethanesulfonic acid containing a phosphatase inhibitor (1 mM okadaic acid; manufactured by Seikagaku Kogyo) and a protease inhibitor (1 mM phenylmethylsulfonyl fluoride and each 1 micro gram/ml of leupeptin, pepstatin and aprotinin), homogenized and centrifuged at 14,000 rpm for one hour and the supernatant liquid was used for checking the phosphorylation.

The rat tau-protein expressed in *E. coli* BL21 by a gene recombination was purified by a method described in J. Biol. Chem., 267, 10897–10901 (1992).

The hippocampus extract (1 microliter) was added to a solution of the rat tau-protein (400 micrograms/ml) dissolved in a buffer A containing 1mM [$\tau$-$^{32}$P]ATP (10–20 Ci/mmole) and then 10 micromoles of okadaic acid was added to make the final volume 10 microliters. This was incubated at 37° C. for three hours and the reaction was stopped by adding a buffer for electrophoresis. After subjecting to a 10% polyacrylamide gel electrophoresis, the $^{32}$p in the tau-protein was observed by a laser image analyzer (Fuji BAS 2000).

Immunohistochemistry by an Alz-50 Antibody:

The cultured medium of the hippocampus cells was fixed in a phosphate buffer for ten minutes using 4% paraformaldehyde. The fixed culture liquid was incubated for 30 minutes in a Tris buffer containing 0.2% Triton X-100 so that the cells were made permeable.

Then this culture medium was subjected to an immunolabelling using a 1:5 diluted Alz-50 mouse monoclonal antibody [Science, 232, 648–650 (1986)], Vectastain ABC avidin-biotin-enzyme peroxide detector kit (manufactured by Vector Laboratory) and diaminobenzidine tetrahydrochloride as a dye.

EXAMPLE 1.

Preparation of Culture Medium of Cells:

The primary culture medium of hippocampus of rats was prepared in accordance with a method described in Brain Res., 126, 397–425 (1977). Thus, the hippocampus tissues were collected from embryo of the rats of 18 days after fertilization and digested in papain (protease) (10 U/ml) at 37° C. for 20 minutes. The resulting cells were added to a Dulbecco's modified Eagle's medium supplied with 5% bovine fetus serum, 5% horse serum, 10 micrograms/ml insulin, 0.1 mg/ml transferrin, 1 microgram/ml aprotinin, 1 mM sodium pyruvate and 84 micrograms/ml gentamycin. This was planted to a well for tissue culture covered with poly-L-lysine at the density of $2 \times 10^5$ cells/cm$^2$, cultured for three days and treated with 1 micromole of cytosine-beta-arabinofuranoside for 24 hours and the cells of the fifth day of the culture were used.

Preparation of AβP:

AβP peptide (SEQ. I.D. NO: 3 of the Sequence Listing) comprising the already-mentioned 43 amino acid residues was synthesized by a method which was described in Science, 250, 279–282(1990) and Proc. Natl. Acad. Sci. USA, 87, 9020–9023(1990) and, after being purified, it was dissolved in 35% acetonitrile to prepare a stock solution of 2M.

Preparation of TPKI-Sense and TPKI-Antisense:

Rat GSK-3β [EMBO J., 9, 2431–2438(1990)], i.e. the TPKI-sense comprising the following 18 bases corresponding to the translation initiating domain of the primary structure of rat TPK-I (FEBS Lett., 325, 167–172 (1993)) and the TPKI-antisense which is complementary thereto were synthesized using an automatic DNA synthesizer (MilliGen), recovered from 20% acrylamide-urea gel and purified by means of an ethanol precipitating method and the precipitate was dissolved in water to adjust to a concentration of 1 micromole.

TPKI-Sense: 5'-ATGTCGGGGCGACCGAGA-3' (SEQ. I.D. NO: 4 of the Sequence Listing)

TPKI-Antisense: 5'-TCTCGGTCGCCCCGACAT-3' (SEQ. ID No. 5 of the Sequence Listing)

Inhibiting Action for the Death of Cranial Nerve Cells:

The culture medium of the hippocampus prepared by the above-mentioned method was subjected to the following treatments (b) to (d), numbers of the living cells with an elapse of time were counted and the result is given in Table 1.

(a) Nontreated culture medium (control):

(b) TPKI-antisense (1 micromole) was added to 1 ml of the cell culture medium and, after five minutes, 20 micromoles of AβP was added followed by keeping at 37° C. for 24 hours.

(c) AβP (20 micromoles) was added to 1 ml of the cell culture medium followed by keeping at 37° C. for 24 hours.

(d) TPKI-sense (1 micromole) was added to 1 ml of the cell culture medium and, after five minutes, 20 micromoles of AβP was added followed by keeping at 37° C. for 24 hours.

TABLE 1

| Treating Agents | Numbers of Living Cells (%) After | |
|---|---|---|
| | 6 hours | 21 hours |
| (Control) | 100 | 100 |
| AβP + TPKI-Antisense | 83.0 | 72.6 |
| AβP | 41.3 | 25.4 |
| AβP + TPKI-Sense | 49.5 | 17.1 |

Table 1 shows the numbers of the living cells with an elapse of time after the above-mentioned treatments (b), (c) and (d) and the numbers are given in terms of percentages to the control.

As shown in Table 1, the numbers of the living cells after 6 and 21 hours of the treatment of the hippocampus cells with TPKI-antisense and AβB (b) were significantly more than those of the case treated only with AβB (c) and of the case treated with TPKI-sense and AβP (d). This fact clearly shows that the TPKI-antisense significantly inhibits the death of the cells by AβP.

Further, it was clarified by the observations of the above-mentioned cases of (b) to (d) after 24 hours using a phase contrast microscope (magnifying power: 400) that, only in the case of (b) where TPKI-antisense and AβP were acted to the hippocampus cells, the cytotoxicity by AβP was little and similar to the case of the control.

Phosphorylation of tau-Protein:

Phosphorylating activity of the TPK-I was measured by the above-mentioned method for the samples of (1) untreated cell culture medium (control); (2) a sample in which 1 micromole of TPKI-antisense was added to 1 ml of the cell culture medium followed by adding 20 micromoles of AβP after 5 hours; and (3) a sample in which 20 micromoles of AβP was added to 1 ml of the cell culture medium and the result is given in Table 2. The phosphorylating activity of TPK-I in Table 2 shows that (units/mg protein) per mg of the protein in the supernatant liquid wherein one unit is equivalent to the intensity of the radioactivity measured by a laser image analyzer (BAS 2000; Fuji).

TABLE 2

| Treating Agent | Phosphorylating Activity of TPKI (unit/mg protein) |
|---|---|
| (Control) | 39.6 |
| AβP + TPKI-Antisense | 31.6 |
| AβP | 66.2 |

As shown in Table 2, the phosphorylating activity of the case (2) in which TPKI-antisense and AβP were acted on the cell culture medium was only about one-half of that of the case (2) in which only AβP was acted. Thus, it is clear that the TPKI-antisense significantly inhibits the phosphorylating activity of TPK-I by AβP.

Example 2.

Cloning of Human TPK-IcDNA

Commercially-available human fetus brain cDNA library (prepared by inserting a 1:1 mixture of cDNA synthesized from mRNA of human fetus brain using oligo dT and ramdom primer to lamda-ZAPII; manufactured by Strategen) was infected to a host which was *E. coli* XL1-blue [W. O. Bullock, et al: Biotechnique, 5, 376–379(1987)]

to form plaques. The plaques (numbers: 450,000) were screened using a probe which was prepared by a part of the translation domain (170 base pair from the 1137th HindIII site to the 1306th A; SEQ. ID No. 8 of the Sequence Listing) of the rat TPK-IcDNA (SEQ. ID No. 2 of the Sequence Listing) whereby 19 positive clones were obtained. Among those, two clones were subcloned to Bluescript SK (Strategen) and then EcoRI fragments which hybridize with the above probe were subcloned to vector pUC19 [C. Yanisch-Perrou, et al: Gene, 33, 103 (1985)]. The restriction enzyme map of the EcoRI fragments of the two clones prepared as such is given in FIG. 1.

Base sequence was determined for entire domains of the clone #1 by a dideoxy method and it lacked the N-terminal moiety of human TPK-I protein. Total length of clone #2 was 2.2 kilobases and, out of a comparison with the restriction enzyme map, it was presumed to probably contain clone #1. Therefore, the base sequences corresponding to 5'-untranslated domain and N-terminal domain mostly comprising human TPK-I protein were determined by a dideoxy method of Sanger, et al. The base sequence of cDNA out of the both results and the amino acid sequence of TPK-I supposed therefrom are given in SEQ. I.D. NO: 1 of the Sequence Listing.

Further, comparison with the amino acid sequence of the rat TPK-I is given in FIG. 2.

Example 3. Expression of Human TPK-I by Insect Cells.

NruI-EcoRI fragments containing entire length of translation domain of human TPK-IcDNA were inserted to a SmaI-EcoRI part of transfer vector PVL1392 [Invitrogen; N. R. Webb and M. D. Summers: Technique, 173–188(1990)] prepared by insertion of virus-originated DNA fragments containing baculovirus (nuclear polyhedrosis virus) polyhedron gene and promoter thereof into vector PUC8 (E. coli-hosted plasmid vector) whereupon an expression vector PVL-TPKI was prepared.

Cell strain Sf9 originated from ovalium cells of Spodoptera spp. was cultured in a medium for insect cells FNM-FH [This was prepared as follows; thus, 0.35mg/lit of sodium bicarbonate (manufactured by Wako Pure Chemical), 3.3 mg/ml of TC lactalbumin hydrolysate (manufactured by Difco) and 3.3 mg/ml of TC yeast late were added to a Grace's insect medium (Sigma), adjusted to pH 6.2, sterilized and then a heat-processed 10t bovine fetus serum, 50 micrograms/ml of gentamycin sulfate and 2.5 micrograms/ml of amphotericin B were added thereto.] and co-infected with wild baculovirus DNA and vector DNA whereupon a homogeneous recombination between them took place to some extent and, as a result, recombinant virus having a TPK-I expressing system was prepared.

Selection of the wild virus-infected cells and the recombinant virus-infected cells was conducted visually and, as a result of repeated selections for three times, the recombinant virus-infected cells were separated. The virus-containing liquid with high infectivity obtained from the supernatant of the cells was further infected to Sf9 cells and cultured for 72 hours to recover 5×108 cells. They were suspended in 30 ml of a buffer A [comprising 10 mM sodium phosphate (pH: 7.05), 1 mM ethylenediaminetetraacetic acid, 5 mM ethyleneglycol bis(2-amino-ethyl ether) tetra acetate, 2 mM dithiothreitol, 10 mM magnesium chloride, 0.1 sodium orthovanadate, 40 micrograms/ml phenyl methanesulfonyl fluoride, 1 microgram/ml leupeptin, 1 microgram/ml pepstatin and 1 microgram/ml antipain], homogenized and centrifuged at 105 G to recover the supernatant liquid. Then the supernatant was subjected to a phosphocellulose column chromatography (filled with P-11; Whatman) and fractionated with a buffer B [comprising 25 mM tris (hydroxymethyl)aminomethane hydrochloride (pH: 7.5), 1 mM ethylenediaminetetraacetic acid, 1 mM dithiothreitol, 0.1% beta-mercaptoethanol, 5% glycerol and 50 mM sodium chloride] with a gradient of sodium chloride concentrations of 50 mM to 250 mM. Each fraction of the eluate was analyzed by means of an electrophoresis and an immunoblot technique and an anti-TPK-I antibody positive fraction which cross-reacts with an anti-rat TPK-I amino terminal antibody [rabbit antiserum obtained as an antigen by expressing rat TPK-I amino terminal 36 residues (SEQ. I.D. NO: 9 of the Sequence Listing) as an E. coli-hosted vector system as its fused protein with beta-galactosidase] was pooled. This was concentrated by means of an ultrafiltration, subjected to a blue sepharose column chromatography (filled with Blue-Sepharose CL-6B of Farmacia) and fractionated by a buffer C [comprising 20 mM N-2-hydroxyethyl-piperazine-N'-2-ethanesulfonic acid (pH: 7.5), 1 mM ethylenediaminetetraacetic acid, 0.1 mM dithiothreitol and 5% glycerol] with a sodium chloride concentration gradient of 0 to 1M. Anti-TPK-I antibody positive fraction was pooled by analysis of immunoblotting and electrophoresis for each fraction, subjected to an ultrafiltration and dialyzed against a buffer D [comprising 100 mM 2- (N-morpholino) -ethanesulfonic acid (pH: 6.5), 0.5 mM magnesium acetate, 1 mM ethyleneglycol bis(2-aminoethyl ether) tetra acetate, 10% glycerol, 0.02% polyoxyethylenesorbitan monolaurate (Tween 20), 0.1 mM phenylmethanesulfonyl fluoride, 1 microgram/ml pepstatin, 1 microgram/ml antipain, 1 microgram/ml leupeptin and 5 mM beta-mercaptoethanol] to give 1 ml of enzyme liquid. Total protein obtained was 0.4 mg.

Progress of phosphorylation was checked using this enzyme solution by the following two methods.

(Phosphorylating Method I) tau-Protein extracted from bovine brain followed by purification (2 microliters; 1.5 mg/ml concentration) and 1 microliters of the above partially-purified enzyme solution were mixed. To the mixture was added a solution containing 2 mM adenosinetriphosphate and 2 mM magnesium acetate and [gamma-32P] adenosinetriphosphate so that the phosphorylation of tau-protein was conducted at room temperature for 20 hours whereby the amount of phosphoric acid incorporated in tau-protein was evaluated.

(Phosphorylating Method II)

Phosphorylation reaction which was the same as in the method I was conducted with an exception that no [gamma-32P]adenosinetriphosphate was contained followed by subjecting to an SDS electrophoresis to blot to nitrocellulose. The blotted tau-protein was subjected to an immunodyeing with anti-tau antibody (rabbit antiserum to chicken fetus brain-originated tau-protein) and anti-p-tau antibody [Ihara, et al: J. Biochem., 99, 1807–1910(1986)].

As a result of the method I, incorporation of tau-protein into phosphoric acid was confirmed while the result of the method II was that:

1) mobility of tau-protein after the reaction was less than that of tau-protein which was not phosphorylated; and
2) tau-protein which was not phosphorylated did not react with anti-p-tau antibody while tau-protein after the reaction reacted with anti-p-tau antibody.

Those results indicate that the outcome was the same as that in the phosphorylation of tau-protein using the TPK-I purified from animal brain.

Example 4. Phosphorylation of Peptide by Recombinant Human TPK-I.

Peptide (hereinafter, abbreviated as "K2") represented by the amino acid sequence described in the SEQ. ID No. 10 of the Sequence Listing was synthesized. This peptide was phosphorylated by the same manner as in the phosphorylating method II in Example 3 with an exception that tau-protein kinase II (TPK-II) purified from bovine brain microtubule was used instead of TPK-I whereupon phosphorylated peptide (hereinafter, abbreviated as "p-K2") was obtained.

Phosphorylations of K2 and p-K2 were conducted according to a phosphorylating method I of Example 3 using human-originated partially purified TPK-I prepared in Example 3 whereupon the progress of phosphorylation of p-K2 was clearly noted while phosphorylation of K2 was slow and its initial speed was about one-tenth of that of p-K2.

The result shows that the outcome was the same as the phosphorylation of K2 and p-K2 using TPK-I purified from animal brain.

Example 5. Expression of Recombination of Human TPK-I by *Escherichia coli*.

SacI-EcoRI fragment of human TPK-IcDNA clone #2 obtained in Example 2 was introduced into an SacI-EcoRI part of vector PUC19 [C. Yanisch-Perrou, et al: Gene, 33, 103 (1985)] to prepare pUSE2. In the meanwhile, in order to prepare an NdeI part in an oligonucleotide from 598th to 629th members of cDNA represented by the base sequence described in the SEQ. I.D. NO: 1 of the Sequence Listing, a plus strand oligonucleotide (SEQ. I.D. NO: 11 of the Sequence Listing) wherein CAT was inserted between 613th and 615th member and a minus strand oligonucleotide (SEQ. I.D. NO: 12 of the Sequence Listing) from 1076th to 1047th members were syn- thesized and a cDNA fragment (SEQ. I.D. NO: 13 of the Sequence Listing) ranging from 598th to 1076th members and having NdeI part duplicating with the initiation codon was obtained by a PCR method [Saiki, et al: Nature, 324, 126 (1986)].

Fragments ranging from a 5'-terminal of the cDNA fragment obtained by a PCR method to a SacI part were inserted to SmaI-SacI part of pUSE2. The NdeI-EcoRI fragment of the plasmid vector was introduced into NdeI-BamHI part of pET3C [A. H. Rosen berg, et al: Gene, 56, 125(1987)] which is one of the vectors having *E. coli* T7 polymerase promoter to construct pET3C/TPKI.

pET3C/TPKI was transformed by conventional means using *E. coli* BL21 (DE3) [F. W. Studier and B. A. Moffatt: J. Mol. Biol. 189, 113 (1986)] as a host to prepare a recombinant. The resulting recombinant *E. coli* was cultured at 37° C. until the middle stage of the logarithmic growth phase, kept at 21° C., 0.3 mM (final concentration) of IPTG (isopropyl-beta-D(-)-thiogalactopyranoside) was added and cultured for four hours more. The living cells (5 g) were suspended in 50 ml of a buffer E [comprising 20 mM of 2-(N-morpholino)-ethanesulfonic acid (pH: 6.5), 1 mM of ethylenediaminetetraacetic acid, 5 mM of beta-mercaptoethanol and 50 mM of sodium chloride], disintegrated with ultrasonic wave and centrifuged at 100,000 g for one hour. The supernatant was subjected to a phosphocellulose column chromatography (filled with P-11; Whatman) which was balanced with a buffer E and then subjected to a gradient elution with sodium chloride concentrations of 50 to 500 mM whereby the fraction which was positive to anti-TPK-I antibody was pooled and concentrated. This was dialyzed against a buffer F [comprising 20 mM of N-2-hydroxyethyl-piperazine-N'-2-ethanesulfonic acid (pH: 7.2), 1 mM of ethylene-diaminetetraacetic acid and 5 mM of beta-mercaptoethanol], subjected to a blue sepharose column chromatography (filled with Blue-Sepharose CL-6B of Farmacia) and eluted with a concentration gradient of 0 to 1M of sodium chloride. Anti-TPK-I antibody positive fractions were collected and dialyzed against a buffer D.

Phosphorylation of tau-protein was conducted by the phosphorylating methods I and II by the same manner as in Example 3 using the resulting partially-purified TPK-I. It was found that, as a result of the phosphorylating method I, 1.2 moles of phosphoric acid was incorporated into one molecule of tau-protein while, as a result of the phosphorylating method II, the mobility of electrophoresis of tau-protein after the reaction became small and the reaction with anti-ptau antibody became positive.

When the partially-purified TPK-I was used for phosphorylation of the peptides K2 and p-K2 by the same manner as in Example 4, the phosphorylation of p-Ka proceeded while that of K2 hardly proceeded.

Those results show that the recombinant TPK-I prepared in this example had the same property as that of TPK-I purified from animal brain and of recombinant TPK-I prepared in Example 3.

(Merit of the Invention)

In accordance with the preventive and the therapeutic agent of Alzheimer's disease of the present invention, the phosphorylating activation of tau-protein kinase I by amyloid beta-protein was inhibited whereby the death of the neurons in the brain can be inhibited. Further, it is possible to conduct a screening of the preventive or the therapeutic agent of Alzheimer's disease utilizing the above mechanism.

Moreover, the human-originated TPK-I of the present invention is an enzyme which specifically acts on tau-protein which is suggested to be related to Alzheimer's disease and also to senile dementia of the Alzheimer's disease type and, therefore, its application for to clarification of cause of those diseases and to the investigations for the agents for the prevention and the therapy thereof can be expected.

We claim:

1. An antisense oligonucleotide which inhibits expression of mRNA encoding tau-protein kinase I, which oligonucleotide binds specifically to said mRNA in such a manner that it binds to at least one nucleotide of the portion of said mRNA which is complementary to SEQ. I.D. NO: 5 or 7.

2. The antisense oligonucleotide according to claim 1, which has a size of 15 to 30 oligonucleotides.

3. The antisense oligonucleotide according to claim 1, which binds to at least one nucleotide of the portion of said mRNA which encodes the first six amino acid residues Met-Ser-Gly- Arg-Pro-Arg of tau-protein kinase I shown in SEQ. I.D. NO:14.

4. The antisense oligonucleotide according to claim 1, which is shown in SEQ. I.D. NO: 5 or 7.

5. A composition comprising the antisense oligonucleotide according to claim 1.

6. A composition comprising the antisense oligonucleotide according to claim 2.

7. A composition comprising the antisense oligonucleotide according to claim 2.

8. A composition comprising the antisense oligonucleotide according to claim 3.

* * * * *

UNITED STATES PATENT AND TRADEMARK OFFICE
CERTIFICATE OF CORRECTION

PATENT NO. : 5,837,853
DATED : November 17, 1998
INVENTOR(S) : Akihiko TAKASHIMA et al.

It is certified that error appears in the above-identified patent and that said Letters Patent is hereby corrected as shown below:

On the cover page of the patent, in the heading [30] Foreign Application Priority Date, the date of "Mar. 20, 1993" should be corrected to read -- Mar. 2, 1993 --.

Signed and Sealed this

Thirtieth Day of March, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:

( A ) LENGTH: 2088 base pairs
        ( B ) TYPE: nucleic acid
        ( C ) STRANDEDNESS: double
        ( D ) TOPOLOGY: linear ( i i ) MOLECULE TYPE: cDNA to genomic RNA ( v i ) ORIGINAL SOURCE:
    ( A ) ORGANISM: human being ( x i ) SEQUENCE DESCRIPTION: SEQ ID NO:1:

```
TTACAGGTGT GAGCCACCTC GCCCAGCTGA GTTCAGTATA ATTTTCAATG AGAAACTGAA      60
ATTCAGTTTT ATAATCAAAG AGCATGTTTG CTGAAGCCAT CATTCTCAGC AAACTAATAC     120
AGGGACAGAA AACCAAACAC CGCATGTTCC ACTCATAAGT GGGAGTTGAA CAATGAGAAC     180
ACACGGACAC AGGGAGGGAA ACATCACACA CCAGGGCCTG TCAGGCGGTC AGGGGTAAGG     240
GGAGAGAGAG CATCGAGACA AATATCTAAG GTATGCGGGG CTTAAAACCT AGATGATGGT     300
TGATAGGTGC AGCAAACCAC CATGGCACAT GTATACCTGT GTAACAAACC CGCACGTCCT     360
GCACATGCAT CCCACAACTT AAAGCAAAAT AAAATATAT ATATTTTCA TATTTTCATA       420
TATAATATAT AAATATATAA TTAAGATAAA ATATTACATA TTACATATGT ATAAATTCAT     480
ATATAACATA TAAAATATAT AATATTATAT ATTATATACA TGTGTATATA AAATCTGGCT     540
GCGGAGTTTT TGATCTATAC ATTGAACAAA TTGTCTCACC TACTGATGAA AAGGTGATTC     600
GCGAAGAGAG TGATC ATG TCA GGG CGG CCC AGA ACC ACC TCC TTT GCG GAG     651
                Met Ser Gly Arg Pro Arg Thr Thr Ser Phe Ala Glu
                 1               5                  10
```

```
AGC TGC AAG CCG GTG CAG CAG CCT TCA GCT TTT GGC AGC ATG AAA GTT     699
Ser Cys Lys Pro Val Gln Gln Pro Ser Ala Phe Gly Ser Met Lys Val
         15                  20                  25

AGC AGA GAC AAG GAC GGC AGC AAG GTG ACA ACA GTG GTG GCA ACT CCT     747
Ser Arg Asp Lys Asp Gly Ser Lys Val Thr Thr Val Val Ala Thr Pro
         30                  35                  40

GGG CAG GGT CCA GAC AGG CCA CAA GAA GTC AGC TAT ACA GAC ACT AAA     795
Gly Gln Gly Pro Asp Arg Pro Gln Glu Val Ser Tyr Thr Asp Thr Lys
 45                  50                  55                  60

CTC ATT GGA AAT GGA TCA TTT GGT GTG GTA TAT CAA GCC AAA CTT TGT     843
Leu Ile Gly Asn Gly Ser Phe Gly Val Val Tyr Gln Ala Lys Leu Cys
                 65                  70                  75

GAT TCA GGA GAA CTG GTC GCC ATC AAG AAA GTA TTG CAG GAC AAG AGA     891
Asp Ser Gly Glu Leu Val Ala Ile Lys Lys Val Leu Gln Asp Lys Arg
         80                  85                  90

TTT AAG AAT CGA GAG CTC CAG ATC ATG AGA AAG CTA GAT CAC TGT AAC     939
Phe Lys Asn Arg Glu Leu Gln Ile Met Arg Lys Leu Asp His Cys Asn
         95                 100                 105

ATA GTC CGA TTG CGT TAT TTC TTC TAC TCC AGT GGT GAG AAG AAA GAT     987
Ile Val Arg Leu Arg Tyr Phe Phe Tyr Ser Ser Gly Glu Lys Lys Asp
     110                 115                 120

GAG GTC TAT CTT AAT CTG GTG CTG GAC TAT GTT CCG GAA ACA GTA TAC    1035
Glu Val Tyr Leu Asn Leu Val Leu Asp Tyr Val Pro Glu Thr Val Tyr
125                 130                 135                 140

AGA GTT GCC AGA CAC TAT AGT CGA GCC AAA CAG ACG CTC CCT GTG ATT    1083
Arg Val Ala Arg His Tyr Ser Arg Ala Lys Gln Thr Leu Pro Val Ile
                145                 150                 155

TAT GTC AAG TTG TAT ATG TAT CAG CTG TTC CGA AGT TTA GCC TAT ATC    1131
Tyr Val Lys Leu Tyr Met Tyr Gln Leu Phe Arg Ser Leu Ala Tyr Ile
            160                 165                 170

CAT TCC TTT GGA ATC TGC CAT CGG GAT ATT AAA CCG CAG AAC CTC TTG    1179
His Ser Phe Gly Ile Cys His Arg Asp Ile Lys Pro Gln Asn Leu Leu
        175                 180                 185

TTG GAT CCT GAT ACT GCT GTA TTA AAA CTC TGT GAC TTT GGA AGT GCA    1227
Leu Asp Pro Asp Thr Ala Val Leu Lys Leu Cys Asp Phe Gly Ser Ala
        190                 195                 200
```

| | | | | | | | | | | | | | | | | |
|---|---|---|---|---|---|---|---|---|---|---|---|---|---|---|---|---|
| AAG | CAG | CTG | GTC | CGA | GGA | GAA | CCC | AAT | GTT | TCG | TAT | ATC | TGT | TCT | CGG | 1275 |
| Lys | Gln | Leu | Val | Arg | Gly | Glu | Pro | Asn | Val | Ser | Tyr | Ile | Cys | Ser | Arg | |
| 205 | | | | 210 | | | | | 215 | | | | | | 220 | |
| TAC | TAT | AGG | GCA | CCA | GAG | TTG | ATC | TTT | GGA | GCC | ACT | GAT | TAT | ACC | TCT | 1323 |
| Tyr | Tyr | Arg | Ala | Pro | Glu | Leu | Ile | Phe | Gly | Ala | Thr | Asp | Tyr | Thr | Ser | |
| | | | | 225 | | | | | 230 | | | | | 235 | | |
| AGT | ATA | GAT | GTA | TGG | TCT | GCT | GGC | TGT | GTG | TTG | GCT | GAG | CTG | TTA | CTA | 1371 |
| Ser | Ile | Asp | Val | Trp | Ser | Ala | Gly | Cys | Val | Leu | Ala | Glu | Leu | Leu | Leu | |
| | | | 240 | | | | | 245 | | | | | 250 | | | |
| GGA | CAA | CCA | ATA | TTT | CCA | GGG | GAT | AGT | GGT | GTG | GAT | CAG | TTG | GTA | GAA | 1419 |
| Gly | Gln | Pro | Ile | Phe | Pro | Gly | Asp | Ser | Gly | Val | Asp | Gln | Leu | Val | Glu | |
| | | 255 | | | | | 260 | | | | | 265 | | | | |
| ATA | ATC | AAG | GTC | CTG | GGA | ACT | CCA | ACA | AGG | GAG | CAA | ATC | AGA | GAA | ATG | 1467 |
| Ile | Ile | Lys | Val | Leu | Gly | Thr | Pro | Thr | Arg | Glu | Gln | Ile | Arg | Glu | Met | |
| | 270 | | | | | 275 | | | | | 280 | | | | | |
| AAC | CCA | AAC | TAC | ACA | GAA | TTT | AAA | TTC | CCT | CAA | ATT | AAG | GCA | CAT | CCT | 1515 |
| Asn | Pro | Asn | Tyr | Thr | Glu | Phe | Lys | Phe | Pro | Gln | Ile | Lys | Ala | His | Pro | |
| 285 | | | | | 290 | | | | | 295 | | | | | 300 | |
| TGG | ACT | AAG | GTC | TTC | CGA | CCC | CGA | ACT | CCA | CCG | GAG | GCA | ATT | GCA | CTG | 1563 |
| Trp | Thr | Lys | Val | Phe | Arg | Pro | Arg | Thr | Pro | Pro | Glu | Ala | Ile | Ala | Leu | |
| | | | | 305 | | | | | 310 | | | | | 315 | | |
| TGT | AGC | CGT | CTG | CTG | GAG | TAT | ACA | CCA | ACT | GCC | CGA | CTA | ACA | CCA | CTG | 1611 |
| Cys | Ser | Arg | Leu | Leu | Glu | Tyr | Thr | Pro | Thr | Ala | Arg | Leu | Thr | Pro | Leu | |
| | | | 320 | | | | | 325 | | | | | 330 | | | |
| GAA | GCT | TGT | GCA | CAT | TCA | TTT | TTT | GAT | GAA | TTA | CGG | GAC | CCA | AAT | GTC | 1659 |
| Glu | Ala | Cys | Ala | His | Ser | Phe | Phe | Asp | Glu | Leu | Arg | Asp | Pro | Asn | Val | |
| | | 335 | | | | | 340 | | | | | 345 | | | | |
| AAA | CTA | CCA | AAT | GGG | CGA | GAC | ACA | CCT | GCA | CTC | TTC | AAC | TTC | ACC | ACT | 1707 |
| Lys | Leu | Pro | Asn | Gly | Arg | Asp | Thr | Pro | Ala | Leu | Phe | Asn | Phe | Thr | Thr | |
| | 350 | | | | | 355 | | | | | 360 | | | | | |
| CAA | GAA | CTG | TCA | AGT | AAT | CCA | CCT | CTG | GCT | ACC | ATC | CTT | ATT | CCT | CCT | 1755 |
| Gln | Glu | Leu | Ser | Ser | Asn | Pro | Pro | Leu | Ala | Thr | Ile | Leu | Ile | Pro | Pro | |
| 365 | | | | | 370 | | | | | 375 | | | | | 380 | |
| CAT | GCT | CGG | ATT | CAA | GCA | GCT | GCT | TCA | ACC | CCC | ACA | AAT | GCC | ACA | GCA | 1803 |
| His | Ala | Arg | Ile | Gln | Ala | Ala | Ala | Ser | Thr | Pro | Thr | Asn | Ala | Thr | Ala | |
| | | | | 385 | | | | | 390 | | | | | 395 | | |
| GCG | TCA | GAT | GCT | AAT | ACT | GGA | GAC | CGT | GGA | CAG | ACC | AAT | AAT | GCT | GCT | 1851 |
| Ala | Ser | Asp | Ala | Asn | Thr | Gly | Asp | Arg | Gly | Gln | Thr | Asn | Asn | Ala | Ala | |
| | | | 400 | | | | | 405 | | | | | 410 | | | |
| TCT | GCA | TCA | GCT | TCC | AAC | TCC | ACC | TGA | ACAGTC | CCGAGCAGCC | AGCTGCACAG | | | | | 1904 |
| Ser | Ala | Ser | Ala | Ser | Asn | Ser | Thr | | | | | | | | | |
| | | 415 | | | | | 420 | | | | | | | | | |
| GAAAAACCAC | CAGTTACTTG | AGTGTCACTC | AGCAACACTG | GTCACGTTTG | GAAAGAATAT | | | | | | | | | | | 1964 |
| TAAAAGAGA | AAAAAATCCT | GTTCATTTTA | GTGTTCAATT | TTTTTATTAT | TATTGTTGTT | | | | | | | | | | | 2024 |
| CTTATTTAAC | CTTGTAAAAT | ATCTATAAAT | ACAAACCAAT | TTCATTGTAT | TCTCACTTTG | | | | | | | | | | | 2084 |
| AGGG | | | | | | | | | | | | | | | | 2088 |

( 2 ) INFORMATION FOR SEQ ID NO:2:

( i ) SEQUENCE CHARACTERISTICS:
        ( A ) LENGTH: 1972 base pairs
        ( B ) TYPE: nucleic acid
        ( C ) STRANDEDNESS: double
        ( D ) TOPOLOGY: linear ( i i ) MOLECULE TYPE: cDNA to genomic RNA ( v i ) ORIGINAL SOURCE:
        ( A ) ORGANISM: rat ( x i ) SEQUENCE DESCRIPTION: SEQ ID NO:2:

```
GGCCAAGAGA  ACGAAGTCTT  TTTTTTTTTT  TTCTTGCGGG  AGAACTTAAT  GCTGCATTTA         60

TTATTAACCT  AGTACCCTAA  CATAAAACAA  AAGGAAGAAA  AGGATTAAGG  AAGGAAAAGG        120

TGAATCGAGA  AGAGCCATC  ATG TCG GGG CGA CCG AGA ACC ACC TCC TTT GCG            172
                       Met Ser Gly Arg Pro Arg Thr Thr Ser Phe Ala
                        1               5                      10

GAG AGC TGC AAG CCA GTG CAG CAG CCT TCA GCT TTT GGT AGC ATG AAA               220
Glu Ser Cys Lys Pro Val Gln Gln Pro Ser Ala Phe Gly Ser Met Lys
            15                  20                  25

GTT AGC AGA GAT AAA GAT GGC AGC AAG GTA ACC ACA GTG GTG GCA ACT               268
Val Ser Arg Asp Lys Asp Gly Ser Lys Val Thr Thr Val Val Ala Thr
        30              35                  40

CCT GGA CAG GGT CCT GAC AGG CCA CAG GAA GTC AGT TAC ACA GAC ACT               316
Pro Gly Gln Gly Pro Asp Arg Pro Gln Glu Val Ser Tyr Thr Asp Thr
    45              50                  55

AAA GTC ATT GGA AAT GGG TCA TTT GGT GTG GTA TAT CAA GCC AAA CTT               364
Lys Val Ile Gly Asn Gly Ser Phe Gly Val Val Tyr Gln Ala Lys Leu
60              65                  70                      75

TGT GAC TCA GGA GAA CTG GTG GCC ATC AAG AAA GTT CTT CAG GAC AAG               412
Cys Asp Ser Gly Glu Leu Val Ala Ile Lys Lys Val Leu Gln Asp Lys
            80                  85                  90

CGA TTT AAG AAC CGA GAG CTC CAG ATC ATG AGA AAG CTA GAT CAC TGT               460
Arg Phe Lys Asn Arg Glu Leu Gln Ile Met Arg Lys Leu Asp His Cys
        95              100                 105

AAC ATA GTC CGA TTG CGG TAT TTC TTC TAC TCG AGT GGC GAG AAG AAA               508
Asn Ile Val Arg Leu Arg Tyr Phe Phe Tyr Ser Ser Gly Glu Lys Lys
    110                 115                 120

GAT GAG GTC TAC CTT AAC CTG GTG CTG GAC TAT GTT CCG GAA ACA GTG               556
Asp Glu Val Tyr Leu Asn Leu Val Leu Asp Tyr Val Pro Glu Thr Val
125                 130                 135

TAC AGA GTC GCC AGA CAC TAT AGT CGA GCC AAG CAG ACA CTC CCT GTG               604
Tyr Arg Val Ala Arg His Tyr Ser Arg Ala Lys Gln Thr Leu Pro Val
140             145                 150                     155

ATC TAT GTC AAG TTG TAT ATG TAC CAG CTG TTC AGA AGT CTA GCC TAT               652
Ile Tyr Val Lys Leu Tyr Met Tyr Gln Leu Phe Arg Ser Leu Ala Tyr
            160                 165                     170

ATC CAT TCC TTT GGG ATC TGC CAT CGA GAC ATT AAA CCA CAG AAC CTC               700
Ile His Ser Phe Gly Ile Cys His Arg Asp Ile Lys Pro Gln Asn Leu
        175                 180                 185

TTG CTG GAT CCT GAT ACA GCT GTA TTA AAA CTC TGC GAC TTT GGA AGT               748
Leu Leu Asp Pro Asp Thr Ala Val Leu Lys Leu Cys Asp Phe Gly Ser
    190                 195                 200

GCA AAG CAG CTG GTC CGA GGA GAG CCC AAT GTT TCA TAT ATC TGT TCT               796
Ala Lys Gln Leu Val Arg Gly Glu Pro Asn Val Ser Tyr Ile Cys Ser
205                 210                 215

CGG TAC TAC AGG GCA CCA GAG CTG ATC TTT GGA GCC ACC GAT TAC ACG               844
Arg Tyr Tyr Arg Ala Pro Glu Leu Ile Phe Gly Ala Thr Asp Tyr Thr
220                 225                 230                 235

TCT AGT ATA GAT GTA TGG TCT GCA GGC TGT GTG TTG GCT GAA TTG TTG               892
Ser Ser Ile Asp Val Trp Ser Ala Gly Cys Val Leu Ala Glu Leu Leu
            240                 245                 250

CTA GGA CAA CCA ATA TTT CCT GGG GAC AGT GGT GTG GAT CAG TTG GTG               940
Leu Gly Gln Pro Ile Phe Pro Gly Asp Ser Gly Val Asp Gln Leu Val
        255                 260                 265

GAA ATA ATA AAG GTC CTA GGA ACA CCA ACA AGG GAG CAA ATT AGA GAA               988
Glu Ile Ile Lys Val Leu Gly Thr Pro Thr Arg Glu Gln Ile Arg Glu
    270                 275                 280

ATG AAC CCA AAT TAT ACA GAA TTC AAA TTC CCC CAA ATC AAG GCA CAT              1036
Met Asn Pro Asn Tyr Thr Glu Phe Lys Phe Pro Gln Ile Lys Ala His
285                 290                 295
```

-continued

| | | | | | | | | | | | | | | | | |
|---|---|---|---|---|---|---|---|---|---|---|---|---|---|---|---|---|
| CCT | TGG | ACG | AAG | GTC | TTT | CGG | CCC | CGA | ACT | CCA | CCA | GAG | GCA | ATC | GCA | 1084 |
| Pro | Trp | Thr | Lys | Val | Phe | Arg | Pro | Arg | Thr | Pro | Pro | Glu | Ala | Ile | Ala | |
| 300 | | | | 305 | | | | | 310 | | | | | | 315 | |
| CTG | TGT | AGC | CGT | CTC | CTG | GAG | TAC | ACG | CCG | ACC | GCC | CGG | CTA | ACA | CCA | 1132 |
| Leu | Cys | Ser | Arg | Leu | Leu | Glu | Tyr | Thr | Pro | Thr | Ala | Arg | Leu | Thr | Pro | |
| | | | | 320 | | | | | 325 | | | | | 330 | | |
| CTG | GAA | GCT | TGT | GCA | CAT | TCA | TTT | TTT | GAT | GAA | TTA | CGG | GAC | CCA | AAT | 1180 |
| Leu | Glu | Ala | Cys | Ala | His | Ser | Phe | Phe | Asp | Glu | Leu | Arg | Asp | Pro | Asn | |
| | | | 335 | | | | | 340 | | | | | 345 | | | |
| GTC | AAA | CTA | CCA | AAT | GGG | CGA | GAC | ACA | CCT | GCC | CTC | TTC | AAC | TTT | ACC | 1228 |
| Val | Lys | Leu | Pro | Asn | Gly | Arg | Asp | Thr | Pro | Ala | Leu | Phe | Asn | Phe | Thr | |
| | | 350 | | | | | 355 | | | | | 360 | | | | |
| ACT | CAA | GAA | CTG | TCA | AGT | AAC | CCA | CCT | CTG | GCC | ACC | ATC | CTT | ATC | CCT | 1276 |
| Thr | Gln | Glu | Leu | Ser | Ser | Asn | Pro | Pro | Leu | Ala | Thr | Ile | Leu | Ile | Pro | |
| | 365 | | | | | 370 | | | | | 375 | | | | | |
| CCT | CAC | GCT | CGG | ATT | CAG | GCA | GCT | GCT | TCA | CCG | CCT | GCA | AAC | GCC | ACA | 1324 |
| Pro | His | Ala | Arg | Ile | Gln | Ala | Ala | Ala | Ser | Pro | Pro | Ala | Asn | Ala | Thr | |
| 380 | | | | | 385 | | | | | 390 | | | | | 395 | |
| GCA | GCC | TCA | GAT | ACT | AAT | GCT | GGA | GAC | CGT | GGA | CAG | ACC | AAT | AAC | GCC | 1372 |
| Ala | Ala | Ser | Asp | Thr | Asn | Ala | Gly | Asp | Arg | Gly | Gln | Thr | Asn | Asn | Ala | |
| | | | | 400 | | | | | 405 | | | | | 410 | | |
| GCT | TCT | GCA | TCA | GCC | TCC | AAC | TCT | ACC | TGA | ACAG | CCCCAAGTAG | CCAGCTGCGC | | | | 1426 |
| Ala | Ser | Ala | Ser | Ala | Ser | Asn | Ser | Thr | | | | | | | | |
| 415 | | | | | 420 | | | | | | | | | | | |

| | | | | | |
|---|---|---|---|---|---|
| AGGGAAGACC | AGCACTTACT | TGAGTGCCAC | TCAGCAACAC | TGGTCACGTT | TGGAAAGAAA | 1486 |
| ATTAAAAAGA | GGAAAACAAA | AACAAAAACA | AAAACCCCG | GCTTTGGTTT | GTTTCTTCTT | 1546 |
| TCTTCTTTTC | CTCTATTTTC | TTTTTAAAA | ATCTGTTTCT | CCTTTTAAAA | AAATTAAGAT | 1606 |
| GAAGTCAAGT | CTGATGTCAT | GGGTAACCCC | ACCTACTTGG | AAGGCTGAGT | CTAGAGGTTT | 1666 |
| ACAGCTCAAG | CCCATGCTGG | ACTACAGTGG | GAGTCCAAGG | CCAGCNTGGG | CAACTTAAAA | 1726 |
| AGAACTTGTT | TCAAAAACGA | CAAAGTTGGC | TGATAATATG | GCTCTCCAAG | AGCCACAATA | 1786 |
| AATAAATATG | TAAATAAACT | CAAATAAGTC | TTGTAATTTA | AATTACACTA | AACTAGGTTA | 1846 |
| ACTTTTAAAC | TCTCATCTTT | AAGAACTACA | GGTTTAAAAA | CCCAACGGTT | GTTTTATGTA | 1906 |
| TTAGGGAAAA | ATGAAAAATC | TAATATAAAA | AGAAGCAGCA | ACAGCAGCAG | GAGCCAACCA | 1966 |
| AAGGAT | | | | | | 1972 |

( 2 ) INFORMATION FOR SEQ ID NO:3:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

| | | | | | | | | | | | | | | |
|---|---|---|---|---|---|---|---|---|---|---|---|---|---|---|
| Asp | Ala | Glu | Phe | Arg | His | Asp | Ser | Gly | Tyr | Glu | Val | His | His | Gln |
| 1 | | | | 5 | | | | | 10 | | | | | 15 |
| Lys | Leu | Val | Phe | Phe | Ala | Glu | Asp | Val | Gly | Ser | Asn | Lys | Gly | Ala |
| | | | | 20 | | | | | 25 | | | | | 30 |
| Ile | Ile | Gly | Leu | Met | Val | Gly | Gly | Val | Val | Ile | Ala | Thr | | |
| | | | | 35 | | | | | 40 | | | | | |

( 2 ) INFORMATION FOR SEQ ID NO:4:

( i ) SEQUENCE CHARACTERISTICS:
        ( A ) LENGTH: 18 bases
        ( B ) TYPE: nucleic acid ( C ) STRANDEDNESS: single
( D ) TOPOLOGY: linear ( i i ) MOLECULE TYPE: other nucleic acid - synthetic DNA (sense primer)

( x i ) SEQUENCE DESCRIPTION: SEQ ID NO:4:

ATGTCGGGGC GACCGAGA 18

( 2 ) INFORMATION FOR SEQ ID NO:5:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( i i ) MOLECULE TYPE: other nucleic acid - synthetic DNA (antisense primer)

( i v ) ANTI-SENSE: yes ( x i ) SEQUENCE DESCRIPTION: SEQ ID NO:5:

TCTCGGTCGC CCCGACAT 18

( 2 ) INFORMATION FOR SEQ ID NO:6:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( i i ) MOLECULE TYPE: other nucleic acid - synthetic DNA (sense primer)

( x i ) SEQUENCE DESCRIPTION: SEQ ID NO:6:

ATGTCAGGGC GGCCCAGA 18

( 2 ) INFORMATION FOR SEQ ID NO:7:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( i i ) MOLECULE TYPE: other nucleic acid - synthetic DNA (anti sense primer)

( i v ) ANTI-SENSE: yes ( x i ) SEQUENCE DESCRIPTION: SEQ ID NO:7:

TCTGGGCCGC CCTGACAT 18

( 2 ) INFORMATION FOR SEQ ID NO:8:

( i ) SEQUENCE CHARACTERISTICS:
( A ) LENGTH: 170 bases
( B ) TYPE: nucleic acid
( C ) STRANDEDNESS: single
( D ) TOPOLOGY: linear ( i i ) MOLECULE TYPE: other nucleic acid ( v i ) ORIGINAL SOURCE:
( A ) ORGANISM: rat ( x i ) SEQUENCE DESCRIPTION: SEQ ID NO:8:

AAGCTTGTGC ACATTCATTT TTTGATGAAT TACGGGACCC AAATGTCAAA CTACCAAATG 60

GGCGAGACAC ACCTGCCCTC TTCAACTTTA CCACTCAAGA ACTGTCAAGT AACCCACCTC    120

TGGCCACCAT CCTTATCCCT CCTCACGCTC GGATTCAGGC AGCTGCTTCA    170

(2) INFORMATION FOR SEQ ID NO:9:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: rat (xi) SEQUENCE DESCRIPTION: SEQ ID NO:9:

Met Ser Gly Arg Pro Arg Thr Thr Ser Phe Ala Glu Ser Cys Lys Pro
 1              5                    10                 15

Val Gln Gln Pro Ser Ala Phe Gly Ser Met Lys Val Ser Arg Asp Lys
          20                      25                  30

Asp Gly Ser Lys
        35

(2) INFORMATION FOR SEQ ID NO:10:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ser Gly Asp Arg Ser Gly Tyr Ser Ser Pro Gly Ser Pro Gly Thr Pro
 1              5                    10                 15

Gly Ser Arg Ser Arg Thr Pro Ser Leu Pro Thr Pro Pro Thr Arg Glu
          20                      25                  30

Pro Lys (2) INFORMATION FOR SEQ ID NO:11:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: other nucleic acid - synthetic DNA (sense
        primer)

(xi) SEQUENCE DESCRIPTION: SEQ ID NO:11:

TTCGCGAAGA GAGTGCATAT GTCAGGGCGG CC    32

(2) INFORMATION FOR SEQ ID NO:12:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: other nucleic acid - synthetic DNA (antisense
        primer)

(iv) ANTI-SENSE: yes ( x i ) SEQUENCE DESCRIPTION: SEQ ID NO:12:

GGGAGCGTCT GTTTGGCTCG ACTATAGTGT 30

( 2 ) INFORMATION FOR SEQ ID NO:13:

( i ) SEQUENCE CHARACTERISTICS:
        ( A ) LENGTH: 479 base pairs
        ( B ) TYPE: nucleic acid
        ( C ) STRANDEDNESS: double
        ( D ) TOPOLOGY: linear ( i i ) MOLECULE TYPE: cDNA to genomic RNA ( v i ) ORIGINAL SOURCE:
        ( A ) ORGANISM: human being ( x i ) SEQUENCE DESCRIPTION: SEQ ID NO:13:

| | | | | | |
|---|---|---|---|---|---|
| TTCGCGAAGA | GAGTGCATAT | GTCAGGGCGG | CCCAGAACCA | CCTCCTTTGC | GGAGAGCTGC | 60 |
| AAGCCGGTGC | AGCAGCCTTC | AGCTTTTGGC | AGCATGAAAG | TTAGCAGAGA | CAAGGACGGC | 120 |
| AGCAAGGTGA | CAACAGTGGT | GGCAACTCCT | GGGCAGGGTC | CAGACAGGCC | ACAAGAAGTC | 180 |
| AGCTATACAG | ACACTAAACT | CATTGGAAAT | GGATCATTTG | GTGTGGTATA | TCAAGCCAAA | 240 |
| CTTTGTGATT | CAGGAGAACT | GGTCGCCATC | AAGAAAGTAT | GCAGGACAA | GAGATTTAAG | 300 |
| AATCGAGAGC | TCCAGATCAT | GAGAAAGCTA | GATCACTGTA | ACATAGTCCG | ATTGCGTTAT | 360 |
| TTCTTCTACT | CCAGTGGTGA | GAAGAAAGAT | GAGGTCTATC | TTAATCTGGT | GCTGGACTAT | 420 |
| GTTCCGGAAA | CAGTATACAG | AGTTGCCAGA | CACTATAGTC | GAGCCAAACA | GACGCTCCC | 479 |

( 2 ) INFORMATION FOR SEQ ID NO:14:

( i ) SEQUENCE CHARACTERISTICS:
        ( A ) LENGTH: 420 amino acids
        ( B ) TYPE: amino acid
        ( C ) STRANDEDNESS: single
        ( D ) TOPOLOGY: linear ( i i ) MOLECULE TYPE:

( v i ) ORIGINAL SOURCE:
        ( A ) ORGANISM: human being ( x i ) SEQUENCE DESCRIPTION: SEQ ID NO:14:

```
                        Met  Ser  Gly  Arg  Pro  Arg  Thr  Thr  Ser  Phe  Ala  Glu
                         1                  5                       10

Ser  Cys  Lys  Pro  Val  Gln  Gln  Pro  Ser  Ala  Phe  Gly  Ser  Met  Lys  Val
          15                  20                      25

Ser  Arg  Asp  Lys  Asp  Gly  Ser  Lys  Val  Thr  Thr  Val  Val  Ala  Thr  Pro
          30                  35                      40

Gly  Gln  Gly  Pro  Asp  Arg  Pro  Gln  Glu  Val  Ser  Tyr  Thr  Asp  Thr  Lys
 45                      50                      55                       60

Leu  Ile  Gly  Asn  Gly  Ser  Phe  Gly  Val  Val  Tyr  Gln  Ala  Lys  Leu  Cys
                65                       70                      75

Asp  Ser  Gly  Glu  Leu  Val  Ala  Ile  Lys  Lys  Val  Leu  Gln  Asp  Lys  Arg
                80                       85                      90

Phe  Lys  Asn  Arg  Glu  Leu  Gln  Ile  Met  Arg  Lys  Leu  Asp  His  Cys  Asn
           95                      100                      105

Ile  Val  Arg  Leu  Arg  Tyr  Phe  Phe  Tyr  Ser  Ser  Gly  Glu  Lys  Lys  Asp
         110                      115                      120

Glu  Val  Tyr  Leu  Asn  Leu  Val  Leu  Asp  Tyr  Val  Pro  Glu  Thr  Val  Tyr
125                       130                      135                      140

Arg  Val  Ala  Arg  His  Tyr  Ser  Arg  Ala  Lys  Gln  Thr  Leu  Pro  Val  Ile
```

|     |     |     | 145 |     |     |     |     | 150 |     |     |     |     | 155 |     |
|-----|-----|-----|-----|-----|-----|-----|-----|-----|-----|-----|-----|-----|-----|-----|
| Tyr | Val | Lys | Leu | Tyr | Met | Tyr | Gln | Leu | Phe | Arg | Ser | Leu | Ala | Tyr | Ile |
|     |     |     | 160 |     |     |     |     | 165 |     |     |     |     | 170 |     |
| His | Ser | Phe | Gly | Ile | Cys | His | Arg | Asp | Ile | Lys | Pro | Gln | Asn | Leu | Leu |
|     |     | 175 |     |     |     |     | 180 |     |     |     |     | 185 |     |     |
| Leu | Asp | Pro | Asp | Thr | Ala | Val | Leu | Lys | Leu | Cys | Asp | Phe | Gly | Ser | Ala |
|     | 190 |     |     |     |     | 195 |     |     |     |     | 200 |     |     |     |     |
| Lys | Gln | Leu | Val | Arg | Gly | Glu | Pro | Asn | Val | Ser | Tyr | Ile | Cys | Ser | Arg |
| 205 |     |     |     |     | 210 |     |     |     |     | 215 |     |     |     |     | 220 |
| Tyr | Tyr | Arg | Ala | Pro | Glu | Leu | Ile | Phe | Gly | Ala | Thr | Asp | Tyr | Thr | Ser |
|     |     |     |     | 225 |     |     |     |     | 230 |     |     |     |     | 235 |     |
| Ser | Ile | Asp | Val | Trp | Ser | Ala | Gly | Cys | Val | Leu | Ala | Glu | Leu | Leu | Leu |
|     |     |     | 240 |     |     |     |     | 245 |     |     |     |     | 250 |     |     |
| Gly | Gln | Pro | Ile | Phe | Pro | Gly | Asp | Ser | Gly | Val | Asp | Gln | Leu | Val | Glu |
|     |     | 255 |     |     |     |     | 260 |     |     |     |     | 265 |     |     |     |
| Ile | Ile | Lys | Val | Leu | Gly | Thr | Pro | Thr | Arg | Glu | Gln | Ile | Arg | Glu | Met |
|     | 270 |     |     |     |     | 275 |     |     |     |     | 280 |     |     |     |     |
| Asn | Pro | Asn | Tyr | Thr | Glu | Phe | Lys | Phe | Pro | Gln | Ile | Lys | Ala | His | Pro |
| 285 |     |     |     |     | 290 |     |     |     |     | 295 |     |     |     |     | 300 |
| Trp | Thr | Lys | Val | Phe | Arg | Pro | Arg | Thr | Pro | Pro | Glu | Ala | Ile | Ala | Leu |
|     |     |     |     | 305 |     |     |     |     | 310 |     |     |     |     | 315 |     |
| Cys | Ser | Arg | Leu | Leu | Glu | Tyr | Thr | Pro | Thr | Ala | Arg | Leu | Thr | Pro | Leu |
|     |     |     | 320 |     |     |     |     | 325 |     |     |     |     | 330 |     |     |
| Glu | Ala | Cys | Ala | His | Ser | Phe | Phe | Asp | Glu | Leu | Arg | Asp | Pro | Asn | Val |
|     |     | 335 |     |     |     |     | 340 |     |     |     |     | 345 |     |     |     |
| Lys | Leu | Pro | Asn | Gly | Arg | Asp | Thr | Pro | Ala | Leu | Phe | Asn | Phe | Thr | Thr |
|     | 350 |     |     |     |     | 355 |     |     |     |     | 360 |     |     |     |     |
| Gln | Glu | Leu | Ser | Ser | Asn | Pro | Pro | Leu | Ala | Thr | Ile | Leu | Ile | Pro | Pro |
| 365 |     |     |     |     | 370 |     |     |     |     | 375 |     |     |     |     | 380 |
| His | Ala | Arg | Ile | Gln | Ala | Ala | Ala | Ser | Thr | Pro | Thr | Asn | Ala | Thr | Ala |
|     |     |     |     | 385 |     |     |     |     | 390 |     |     |     |     | 395 |     |
| Ala | Ser | Asp | Ala | Asn | Thr | Gly | Asp | Arg | Gly | Gln | Thr | Asn | Asn | Ala | Ala |
|     |     |     | 400 |     |     |     |     | 405 |     |     |     |     | 410 |     |     |
| Ser | Ala | Ser | Ala | Ser | Asn | Ser | Thr |     |     |     |     |     |     |     |     |
|     |     | 415 |     |     |     |     | 420 |     |     |     |     |     |     |     |     |